(12) United States Patent
Morin et al.

(10) Patent No.: US 12,108,946 B2
(45) Date of Patent: Oct. 8, 2024

(54) DEVICES AND METHODS FOR OCCLUSION OF VASCULAR SYSTEM ABNORMALITIES

(71) Applicant: St. Jude Medical, Cardiology Division, Inc., St. Paul, MN (US)

(72) Inventors: Kristen Morin, St. Paul, MN (US); Trevor Springer, Stillwater, MN (US); Andrey Samaray, Champlin, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 117 days.

(21) Appl. No.: 17/368,467

(22) Filed: Jul. 6, 2021

(65) Prior Publication Data
US 2022/0008050 A1    Jan. 13, 2022

Related U.S. Application Data

(60) Provisional application No. 63/048,835, filed on Jul. 7, 2020.

(51) Int. Cl.
*A61B 17/00*    (2006.01)

(52) U.S. Cl.
CPC ...... *A61B 17/0057* (2013.01); *A61B 2017/00526* (2013.01); *A61B 2017/00592* (2013.01); *A61B 2017/00623* (2013.01); *A61B 2017/00646* (2013.01); *A61B 2017/00867* (2013.01)

(58) Field of Classification Search
CPC ........ A61B 17/00592; A61B 17/00623; A61B 17/00646; A61B 17/00867
See application file for complete search history.

(56) References Cited

U.S. PATENT DOCUMENTS

| 6,168,622 B1* | 1/2001 | Mazzocchi | ........ A61B 17/0057 623/1.2 |
| 8,961,556 B2* | 2/2015 | Amplatz | .......... A61B 17/12122 606/200 |
| 2002/0099437 A1 | 7/2002 | Anson et al. | |

(Continued)

FOREIGN PATENT DOCUMENTS

| WO | 2013074486 A1 | 5/2013 |
| WO | 2018058033 A1 | 3/2018 |

OTHER PUBLICATIONS

International Search Report and Written Opinion for International Application No. PCT/US2021/040528, mailed Oct. 28, 2021, 18 pages.

*Primary Examiner* — Alexander J Orkin
(74) *Attorney, Agent, or Firm* — Armstrong Teasdale LLP (57) ABSTRACT

Described herein is a medical device for treating a target site, the medical device including, a proximal end including a disc and a distal end including a lobe. The disc and the lobe are connected by a connecting member. The lobe includes a proximal portion defining a proximal surface of the lobe, a distal portion defining a distal surface of the lobe, and a middle portion connecting and extending between the proximal portion and the distal portion. A first transition between the proximal portion and the middle portion is curved, and a second transition between the middle portion and the distal portion is curved. The medical device also includes a plurality of stabilizing wires coupled to the lobe at a radially outer surface of the middle portion, each stabilizing wire including a hook portion extending radially outward from the at least one lobe.

16 Claims, 9 Drawing Sheets

(56) References Cited

U.S. PATENT DOCUMENTS

| | | | |
|---|---|---|---|
| 2007/0167980 A1* | 7/2007 | Figulla | A61B 17/12177 606/213 |
| 2011/0257723 A1* | 10/2011 | McNamara | A61L 31/022 623/1.11 |
| 2012/0065667 A1* | 3/2012 | Javois | A61B 17/12172 606/213 |
| 2013/0131717 A1* | 5/2013 | Glimsdale | A61B 17/12172 606/213 |
| 2013/0165065 A1 | 6/2013 | Jaisimha et al. | |
| 2013/0165965 A1 | 6/2013 | Carlson et al. | |
| 2013/0296912 A1* | 11/2013 | Ottma | A61B 17/0057 606/191 |
| 2014/0005714 A1* | 1/2014 | Quick | A61B 17/12122 606/200 |
| 2014/0142610 A1* | 5/2014 | Larsen | A61B 17/12122 606/200 |
| 2014/0194921 A1* | 7/2014 | Akpinar | A61B 17/12122 606/200 |
| 2015/0005809 A1* | 1/2015 | Ayres | A61F 2/01 606/191 |
| 2016/0030050 A1* | 2/2016 | Franano | A61B 17/1214 606/195 |
| 2018/0193027 A1* | 7/2018 | Wang | A61B 17/12122 |
| 2018/0271540 A1* | 9/2018 | Merritt | A61B 17/12172 |
| 2019/0110796 A1* | 4/2019 | Jayaraman | A61B 17/12168 |

\* cited by examiner

DEVICES AND METHODS FOR OCCLUSION OF VASCULAR SYSTEM ABNORMALITIES

CROSS-REFERENCE TO RELATED APPLICATIONS

This application claims the benefit of priority to U.S. Provisional Patent Application No. 63/048,835, filed Jul. 7, 2020, which is hereby incorporated by reference herein in its entirety.

BACKGROUND OF THE DISCLOSURE

A. Field of Disclosure

The present disclosure relates generally to medical devices that are used in the human body. In particular, the present disclosure is directed to an occlusion device having a more consistent lobe shape when the occlusion device is deployed in the human body. More specifically, the present disclosure is directed to an occlusion device with a rounded lobe and stabilizing wires extending radially outward therefrom. The embodiments and methods disclosed herein enable a more consistent angle of the stabilizing wires and more uniform radial compression when the lobe is compressed during normal sinus rhythm.

B. Background

An occluder is a medical device used to treat (e.g., occlude) tissue at a target site within the human body, such as an abnormality, a vessel, an organ, an opening, a chamber, a channel, a hole, a cavity, a lumen, or the like. For example, an occluder may be used for Left Atrial Appendage (LAA) closures. An LAA is a normal anatomical structure in which there is a sac in the muscle wall of the left atrium. When a patient experiences atrial fibrillation (AFib), a blood clot may be formed within the LAA which may become dislodged and enter into the blood stream. By occluding the LAA, the release of blood clots from the LAA may be significantly reduced, if not eliminated. Various techniques have been developed to occlude the LAA. For instance, balloon-like devices have been developed that are configured to be implanted completely within the cavity of the LAA, while surgical techniques have also been developed where the cavity of the LAA is inverted and surgically closed.

Despite these techniques, it would be advantageous to provide an improved occlusion device that offers a reduced risk of adverse events such as pericardial effusion.

SUMMARY OF THE DISCLOSURE

The present disclosure generally relates to medical devices and methods of manufacturing and use thereof, with a rounded lobe and stabilizing wires extending radially outward therefrom which enables a more consistent angle of the stabilizing wires and more uniform radial compression when the lobe of the medical device is compressed during normal sinus rhythm.

In one embodiment, the present disclosure is directed to a medical device for treating a target site. The medical device includes a proximal and a distal end. The proximal end includes a disc and the distal end includes a lobe. The disc and lobe are connected by a connecting member. The lobe includes a proximal portion defining a proximal surface of the lobe, a distal portion defining a distal surface of the lobe, and a middle portion connecting and extending between the proximal portion and the distal portion. A first transition between the proximal portion and the middle portion is curved and a second transition between the middle portion and the distal portion is curved. The lobe has an expanded configuration when deployed at the target site and a reduced configuration for delivery to the target site. A plurality of stabilizing wires are coupled to the lobe at a radially outer surface of the middle portion, each stabilizing wire includes a hook portion extending radially outward from the at least one lobe.

In another embodiment, a delivery system for deploying a medical device to a target site is provided. The delivery system includes a medical device and a delivery device. The medical device includes a proximal and a distal end. The proximal end includes a disc and the distal end includes a lobe. The disc and the lobe are connected by a connecting member. The lobe includes a proximal portion defining a proximal surface of the lobe, a distal portion defining a distal surface of the lobe, and a middle portion connecting and extending between the proximal portion and the distal portion. A first transition between the proximal portion and the middle portion is curved and a second transition between the middle portion and the distal portion is curved. The lobe has an expanded configuration when deployed at the target site and a reduced configuration for delivery to the target site. A plurality of stabilizing wires are coupled to the lobe at a radially outer surface of the middle portion, each stabilizing wire includes a hook portion extending radially outward from the at least one lobe. The delivery device includes a delivery catheter, a delivery cable within the delivery catheter and translatable with respect to the delivery catheter, and a coupling member configured to couple the medical device to the delivery cable for facilitating at least one deployment of the medical device at the target site.

In a further embodiment, a method for occluding a Left Atrial Appendage is provided. The method includes providing a medical device. The medical device includes a proximal and a distal end. The proximal end includes a disc and the distal end includes a lobe. The disc and the lobe are connected by a connecting member. The lobe includes a proximal portion defining a proximal surface of the lobe, a distal portion defining a distal surface of the lobe, and a middle portion connecting and extending between the proximal portion and the distal portion. A first transition between the proximal portion and the middle portion is curved and a second transition between the middle portion and the distal portion is curved. The lobe has an expanded configuration when deployed at the target site and a reduced configuration for delivery to the target site. A plurality of stabilizing wires are coupled to the lobe at a radially outer surface of the middle portion, each stabilizing wire includes a hook portion extending radially outward from the at least one lobe. The method also includes advancing the medical device to the LAA using the delivery system, positioning the medical device relative to the LAA to occlude blood flow, and de-coupling the medical device from the delivery cable to deploy the medical device.

In a further embodiment, a method of fabricating a medical device is provided. The medical device includes providing a medical device. The medical device includes a proximal and a distal end. The proximal end includes a disc and the distal end includes a lobe. The disc and the lobe are connected by a connecting member. The lobe includes a proximal portion defining a proximal surface of the lobe, a distal portion defining a distal surface of the lobe, and a middle portion connecting and extending between the proximal portion and the distal portion. A first transition between the proximal portion and the middle portion is curved and a second transition between the middle portion and the distal portion is curved. The lobe has an expanded configuration when deployed at the target site and a reduced configuration for delivery to the target site. A plurality of stabilizing wires are coupled to the lobe at a radially outer surface of the middle portion, each stabilizing wire includes a hook portion extending radially outward from the at least one lobe. The method includes providing a shape-memory material, positioning the shape-memory material on a mandrel having a desired shape, size, and radius of curvature for a first transition and a radius of curvature for a second transition, and removing the shape-memory material from the mandrel, and obtaining the medical device.

BRIEF DESCRIPTION OF THE DRAWINGS

Corresponding reference characters indicate corresponding parts throughout the several views of the drawings. It is understood that that Figures are not necessarily to scale.

DETAILED DESCRIPTION OF THE DISCLOSURE

The present disclosure relates generally to medical devices that are used in the human body. Specifically, the present disclosure provides medical devices including occlusion devices having a rounded lobe at a distal end thereof. The rounded shape of the lobe enables the lobe to maintain a more consistent shape in its use range (e.g., under various radial compression forces experienced while the medical device is deployed at a target site). Rounding the edges of the lobe, as described herein, creates a bending moment in a circumferential face of the lobe, such that this circumferential face resists becoming concave. In the exemplary embodiment, the medical device further includes stabilizing wires coupled to the surface of and extending radially outward from the lobe. When the lobe maintains a non-concave shape during sinus compressions, the stabilizing wires maintain a more consistent angle, which in turn maintains an optimal engagement between the stabilizing wires and the adjacent tissue.

Accordingly, the occlusion devices of the present disclosure decrease the motion of the stabilizing wires, which enables the medical device to minimize the retraction of the stabilizing wires from tissue when the device is deployed at the target site.

The disclosed embodiments may lead to more consistent and improved patient outcomes. It is contemplated, however, that the described features and methods of the present disclosure as described herein may be incorporated into any number of systems as would be appreciated by one of ordinary skill in the art based on the disclosure herein.

Although the exemplary embodiment of the medical device is described as treating a target site including a left atrial appendage (LAA), it is understood that the use of the term "target site" is not meant to be limiting, as the medical device may be configured to treat any target site, such as an abnormality, a vessel, an organ, an opening, a chamber, a channel, a hole, a cavity, or the like, located anywhere in the body. The term "vascular abnormality," as used herein is not meant to be limiting, as the medical device may be configured to bridge or otherwise support a variety of vascular abnormalities. For example, the vascular abnormality could be any abnormality that affects the shape of the native lumen, such as an atrial septal defect, a lesion, a vessel dissection, or a tumor. Embodiments of the medical device may be useful, for example, for occluding a patent foramen ovalis (PFO), atrial septal defect (ASD), ventricular septal defect (VSD), or patent ductus arteriosus (PDA), as noted above. Furthermore, the term "lumen" is also not meant to be limiting, as the vascular abnormality may reside in a variety of locations within the vasculature, such as a vessel, an artery, a vein, a passageway, an organ, a cavity, or the like. As used herein, the term "proximal" refers to a part of the medical device or the delivery device that is closest to the operator, and the term "distal" refers to a part of the medical device or the delivery device that is farther from the operator at any given time as the medical device is being delivered through the delivery device. In addition, the terms "deployed" and "implanted" may be used interchangeably herein.

Some embodiments of the present disclosure provide an improved percutaneous catheter directed intravascular occlusion device for use in the vasculature in patients' bodies, such as blood vessels, channels, lumens, a hole through tissue, cavities, and the like, such as an atrial septal defect. Other physiologic conditions in the body occur where it is also desirous to occlude a vessel or other passageway to prevent blood flow into or therethrough. These device embodiments may be used anywhere in the vasculature where the anatomical conditions are appropriate for the design.

The medical device may include one or more layers of occlusive material, wherein each layer may be comprised of any material that is configured to substantially preclude or occlude the flow of blood so as to facilitate thrombosis. As used herein, "substantially preclude or occlude flow" shall mean, functionally, that blood flow may occur for a short time, but that the body's clotting mechanism or protein or other body deposits on the occlusive material results in occlusion or flow stoppage after this initial time period.

Some embodiments of the present disclosure may be formed by a plurality of wire strands having a predetermined relative orientation with respect to one another. However, it is understood that according to additional embodiments of the present disclosure, that the medical device could be etched or laser cut from a tube, or the device could comprise an occlusion material coupled to a scaffolding structure or a plurality of slices of a tubular member coupled together.

The present disclosure now will be described more fully hereinafter with reference to the accompanying drawings, in which some, but not all embodiments of the disclosure are shown. Indeed, this disclosure may be embodied in many different forms and should not be construed as limited to the embodiments set forth herein; rather, these embodiments are provided so that this disclosure will satisfy applicable legal requirements. Like numbers refer to like elements throughout.

Figure 1:
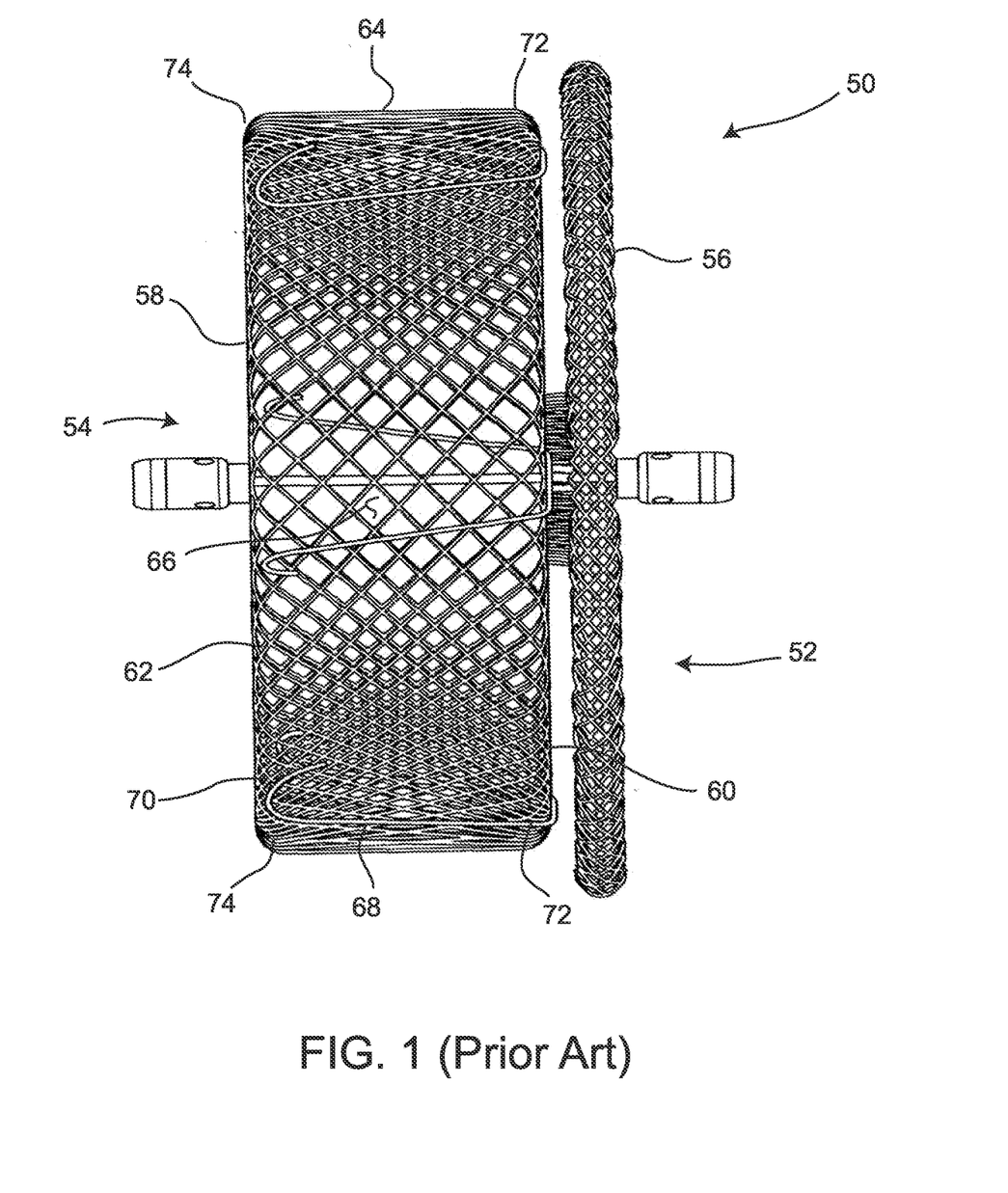
FIG. 1 illustrates a known medical device.

In at least some conventional or known medical devices used for the occlusion of abnormalities, such as a medical device 50 shown in FIG. 1, medical device 50 includes a proximal end 52 and a distal end 54, with a disc 56 at proximal end 52 and a lobe 58 at distal end 54. The lobe 58 has a proximal edge 60 (also referred to as a proximal face), a distal edge 62 (also referred to as a distal face), and a middle or central portion 64 that define a cavity 66. The medical device 50 also includes stabilizing wires 68 secured to a radially outer or circumferential surface of middle portion 64. The stabilizing wires 68 terminate in a hook 70 at free ends thereof, and thereby facilitate retention of the medical device 50 at a target site and preventing the medical device 50 from becoming dislodged from the target site after deployment.

In this known medical device 50, proximal edge 60 and distal edge 62 adjoin middle portion 64 at a first relatively blunt or sharp (i.e., non-rounded) transition 72 and a second blunt transition 74, respectively. First blunt transition 72 connects proximal edge 60 to middle portion 64 by an approximately 90 degree angle. Likewise, second blunt transition 74 connects distal edge 62 to middle portion 64 by an approximately 90 degree angle. First blunt transition 72 and second blunt transition 74 partially define a generally rectangular cross section to lobe 58, leading to relatively blunt circumferential edges of the device and relatively high radial force applied to the surrounding tissue.

Figure 2A:
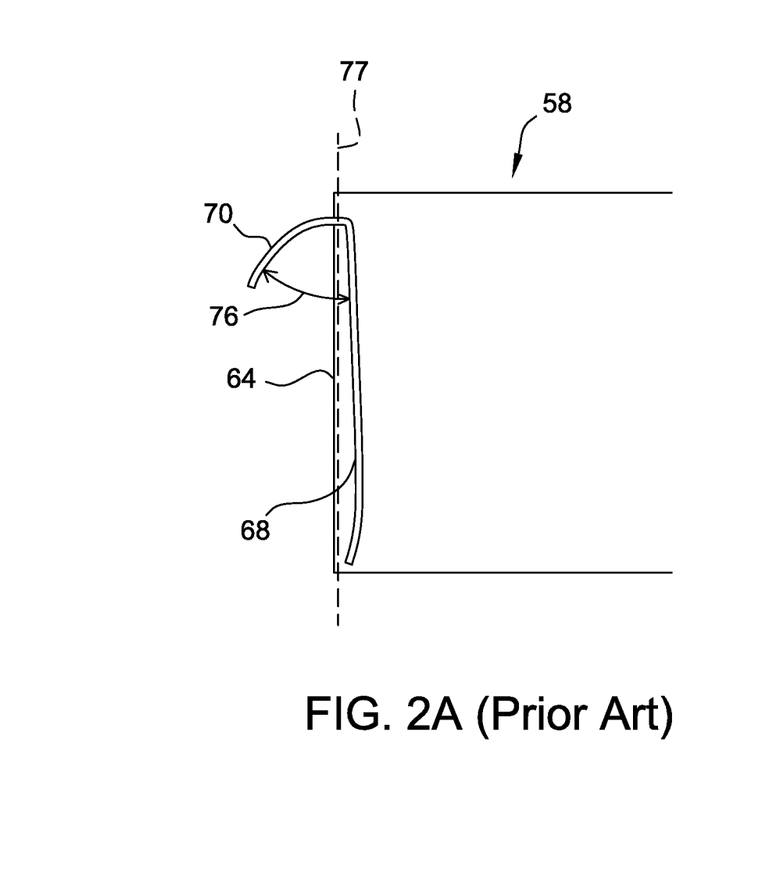
FIGS. 2A-2C are a schematic diagram of the known medical device shown in FIG. 1 under radial compression.
Figure 2B:
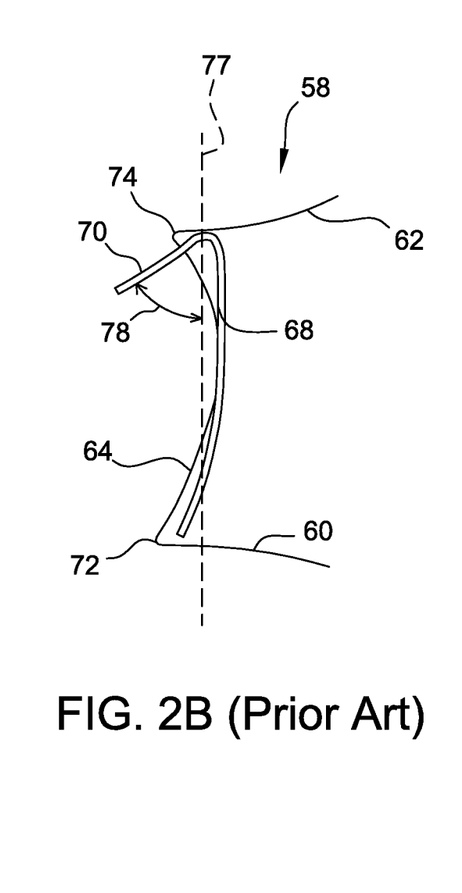
Figure 2C:
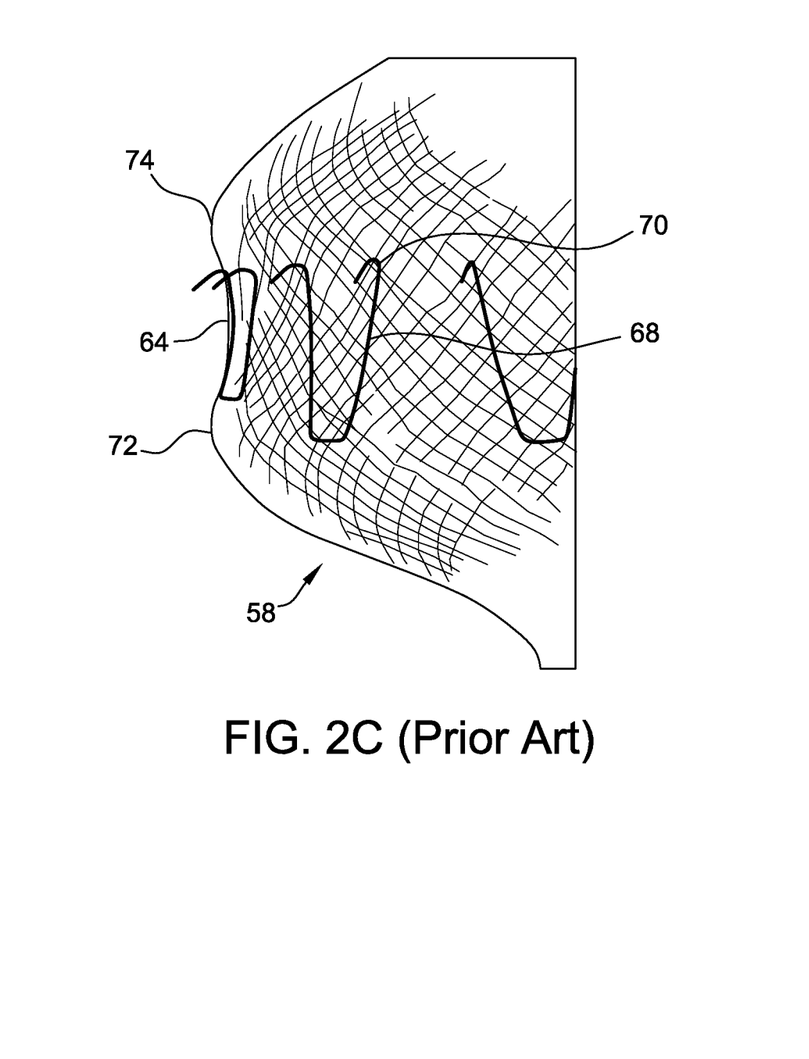

Turning now to FIGS. 2A-2C, medical device 50 before and after undergoing radial compression is depicted. Before radial compression (FIG. 2A) is applied to lobe 58, the outer surface of middle portion 64 is linear or extends generally perpendicular to proximal and distal faces 60, 62. Each hook 70 of a corresponding stabilizing wire 68 is at a first angle 76 with respect to a generally longitudinal direction 77. When radial compression is applied to lobe 58 (FIGS. 2B and 2C), proximal and distal faces 60, 62 flex and bow outwardly (e.g., axially outward), and middle portion 64 of lobe 58 flexes and bows inwardly, in response to the applied force. The approximately 90 degree angle of first blunt transition 72 and second blunt transition 74 force the outer surface of middle portion 64 to transition from linear to concave when proximal and distal faces 60, 62 bow outwardly. The concave shape adopted by lobe 58 also shifts the position of stabilizing wires 68, such that stabilizing wires 68 at least partially contract and hooks 70 transition from first angle 76 to a second, greater angle 78. At second angle 78, hooks 70 are oriented more directly towards the adjacent tissue, than when hooks 70 are at first angle 76. This shift in orientation of stabilizing wires 68, and therefore hooks 70, can lead to an increase in interactions between hooks 70 and the adjacent tissue at the target site within the patient's body. The increased interaction with tissue can lead to adverse side effects such as late pericardial effusion.

The medical devices of the present disclosure, which include a rounded lobe, can lead to a more uniform radial compression, reduction in radial force applied to surrounding tissue, and reduction in variability of the hook angle of the stabilizing wires, minimizing potential disadvantages of known medical devices.

Figure 3:
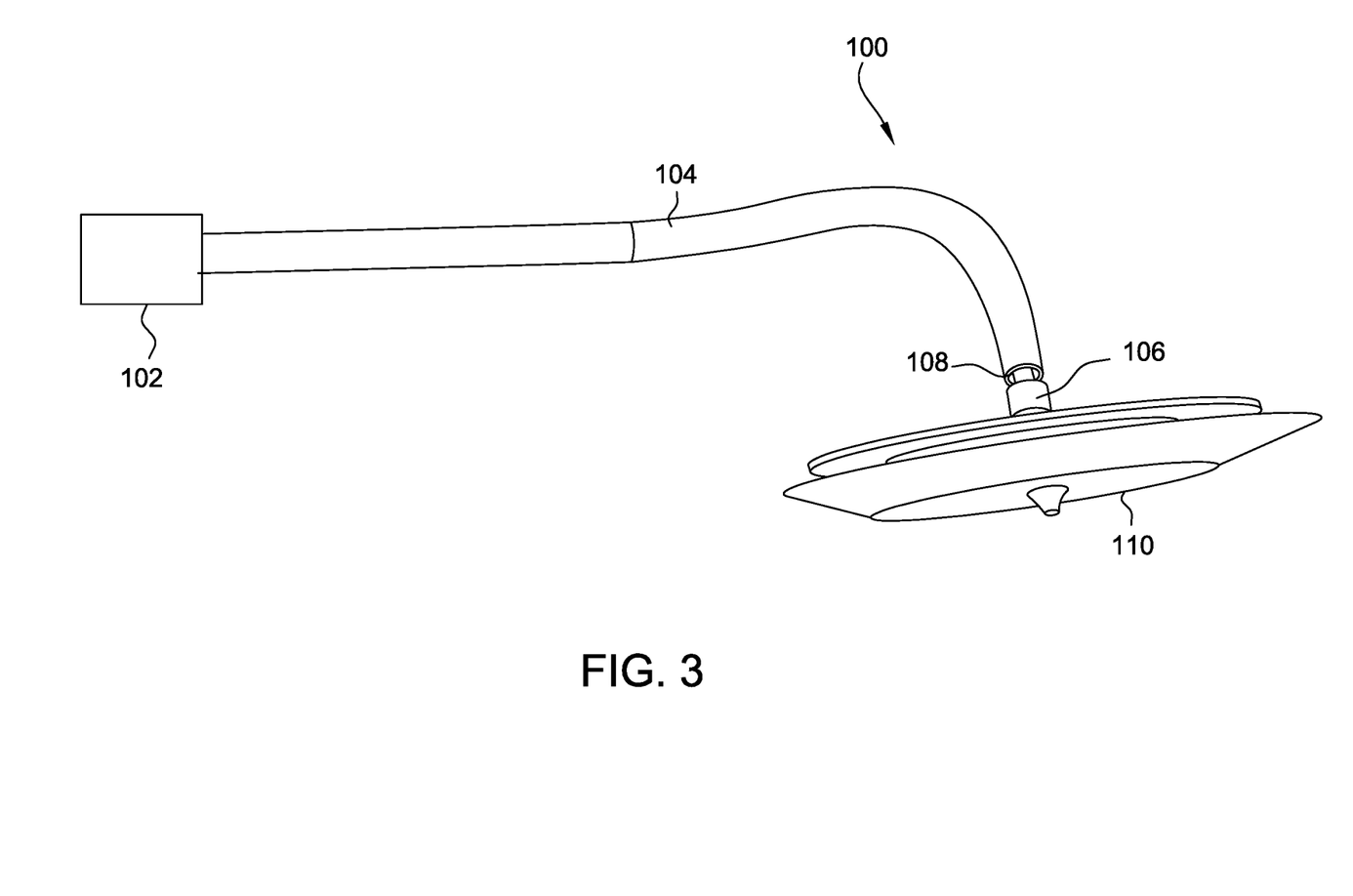
FIG. 3 is a schematic diagram of a delivery system in accordance with the present disclosure.

Turning now to FIG. 3, a schematic diagram of a delivery system 100 is shown. Delivery system 100 includes a delivery device 102 including a catheter 104 and a coupling member 106 configured to couple a distal end of a delivery cable 108 to a medical device 110 for facilitating the deployment of medical device 110 at a target site. Medical device 110 is deployed to treat the target site, and, in the example embodiment, is an occlusion device ("occluder").

Figure 4:
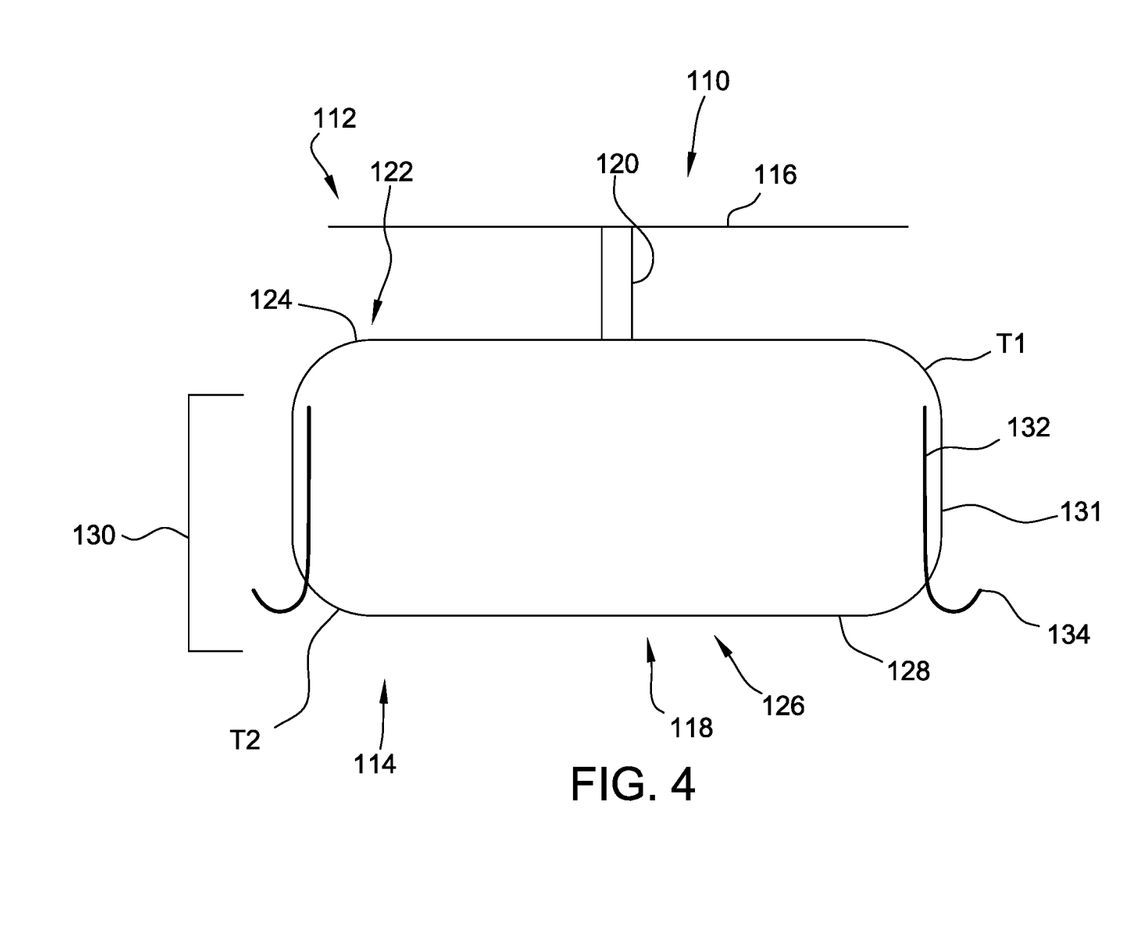
FIG. 4 illustrates a side view of an exemplary embodiment of a medical device including a rounded lobe, in accordance with the present disclosure.

FIG. 4 illustrates an exemplary embodiment of medical device 110. Medical device 110 includes a proximal end 112 and a distal end 114. Proximal end 112 includes a disc 116, and distal end 114 includes a lobe 118, wherein disc 116 and lobe 118 are connected by a connecting member 120. Lobe 118 includes a proximal portion 122 defining a proximal surface 124 of lobe 118, a distal portion 126 defining a distal surface 128 of lobe 118, and a middle or central portion 130 connecting and extending between proximal portion 122 and distal portion 126. Central portion 130 has a circumferential or radially outer surface 131. Proximal surface 124 is connected to or adjoins middle portion 130 at a first transition T1, and distal surface 128 is connected to or adjoins middle portion 130 at a second transition T2. First transition T1 and second transition T2 each independently have a radius of curvature of 0.001 inches to 0.150 inches, more particularly 0.025 inches to 0.150 inches, even more particularly 0.075 inches to 0.125 inches. The radius of curvature of first transition T1 is the same as the radius of curvature of second transition T2. Alternatively, first transition T1 and second transition T2 have different radii of curvature. In one alternative embodiment, only one of first transition T1 and second transition T2 has a defined radius of curvature, and the other is a relatively blunt transition (e.g., approximately 90°).

Lobe further 118 includes a plurality of stabilizing wires 132 coupled to lobe 118 at radially outer surface 131 (also referred to as circumferential surface) of middle portion 130. Stabilizing wires 132 each include a hook 134 at a terminal end therefore. Hooks 134 extend radially outward from middle portion 130 of lobe 118.

Some embodiments of medical device 110 of the present disclosure may be formed from a braided fabric or mesh material including a plurality of wire strands having a predetermined relative orientation with respect to one another. However, it is understood that according to additional embodiments of the present disclosure, medical device 110 could be etched or laser cut from a tube, or the device could comprise an occlusion material coupled to a scaffolding structure or frame.

In one embodiment, medical device 110 is formed from a shape-memory material including a metal fabric. The metal fabric is deformed to generally conform to a surface of a mandrel. While on the surface of the mandrel, the metal fabric is treated under heated conditions to allow for the heat-setting of the metal fabric. The heat-setting of the metal fabric ensures that the metal fabric will retain the substantial shape of the mandrel once it is removed from the surface of the mandrel. In the exemplary embodiment, the mandrel utilized for the heat-setting treatment defines the radii of curvature adopted by the metal fabric for the edges of lobe 118 of medical device 110, specifically first transition T1 and second transition T2.

The radius of curvature selected and defined for each of first transition T1 and second transition T2 rounds or softens the circumferential edges of medical device 110. This rounding or softening of the circumferential edge leads to a reduction in the radial force applied to the surrounding tissue. Therefore, medical device 110 is more conformable to the anatomy of the target site in which it is deployed, specifically an LAA.

Disc 116 of medical device 110 is configured to abut the adjacent wall surrounding the opening of the vascular defect to prevent movement of medical device 110 and to assist in sealing of the abnormality in which medical device 110 is deployed. Different sizes and shapes of the disc are contemplated. In one embodiment, the disc portion may be larger in diameter than the vascular abnormality to be occluded to be capable of overlying the opening of the abnormality.

Lobe 118 of medical device 110 is formed to have a suitable size to engage with the lumen of the abnormality that is to be occluded. Medical device 110 may then be held at the target site by radial engagement between lobe 118 and the lumen of the abnormality. Hooks 134 of stabilizing wires 132 also engage with the surrounding tissue and improve retention of medical device 110 at the target site.

Figure 5A:
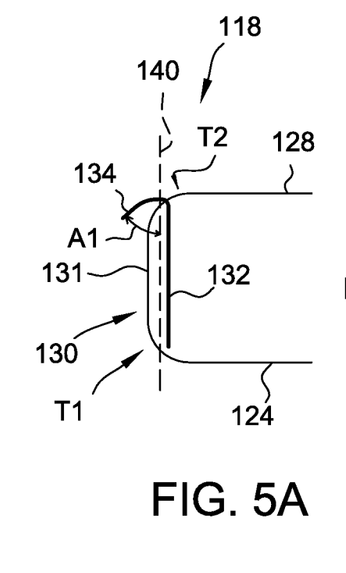
FIGS. 5A and 5B are a schematic diagram of the medical device shown in FIG. 4 under radial compression.
Figure 5B:
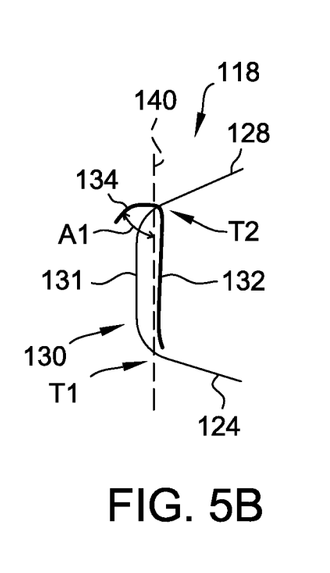
Figure 6:
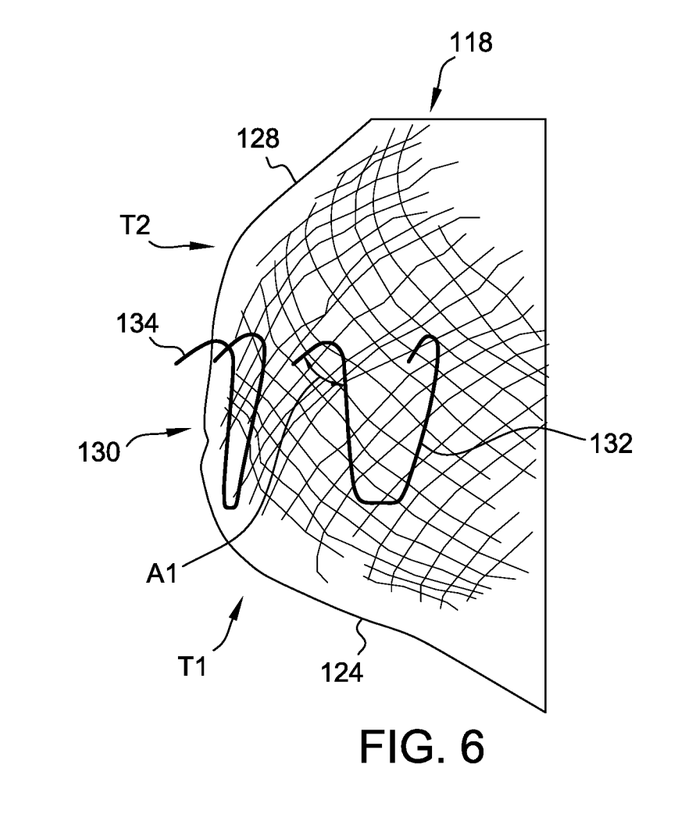
FIG. 6 is an expanded view of the medical device shown in FIG. 4 under radial compression.

In addition to the rounding or softening of the circumferential edges of lobe 118, the rounding of the first and second transitions facilitates more uniform radial compression of lobe 118 when deployed at the target site. FIGS. 5A and 5B illustrate medical device 110 in accordance with the present disclosure undergoing radial compression. Before radial compression is applied to medical device 110 (FIG. 5A), radially outer surface 131 of middle portion 130 is generally linear between first transition T1 and second transition T2. In addition, hooks 134 are oriented at a first angle A1 with respect to a longitudinal direction 140. When radial compression is applied to lobe 118 (FIGS. 5B and 6), proximal surface 124 and distal surface 128 still bow outwardly (e.g., axially or longitudinally outward) in response to the applied force. In response, middle portion 130 may flex but resists bowing radially inward. Specifically, rounded first and second transitions T1, T2 enable proximal surface 124 and distal surface 128 to flex outwardly, without middle portion 130 flexing or compressing in a concave manner, or without middle portion 130 bowing inwardly. Therefore, stabilizing wires 132 are not substantially shifted or contracted, and hooks 134 maintain first angle A1. It is contemplated that hooks 134 may undergo a slight shift, but this shift is minimal and greatly reduced compared to the shift of the hooks in known medical devices, as described above.

One particular shape memory material that may be used to form medical device 110 (and, particularly, lobe 118) as described herein is Nitinol. Nitinol alloys are highly elastic and are said to be "superelastic," or "pseudoelastic." This elasticity may allow medical device 110 to be resilient and return to a preset, expanded configuration for deployment following passage in a distorted form through delivery catheter 104. Further examples of materials and manufacturing methods for medical devices with shape memory properties are provided in U.S. Publication No. 2007/0265656 titled "Multi-layer Braided Structures for Occluding Vascular Defects" and filed on Jun. 21, 2007, which is incorporated by reference herein in its entirety.

It is also understood that medical device 110 may be formed from various materials other than Nitinol that have elastic properties, such as stainless steel, trade named alloys such as Elgiloy®, or Hastalloy, Phynox®, MP35N, CoCrMo alloys, metal, polymers, or a mixture of metal(s) and polymer(s). Suitable polymers may include PET (Dacron), polyester, polypropylene, polyethylene, HDPE, Pebax, nylon, polyurethane, silicone, PTFE, polyolefins and ePTFE. Additionally, it is contemplated that the medical device may comprise any material that has the desired elastic properties to ensure that the device may be deployed, function as an occluder as disclosed within this application.

Figure 7:
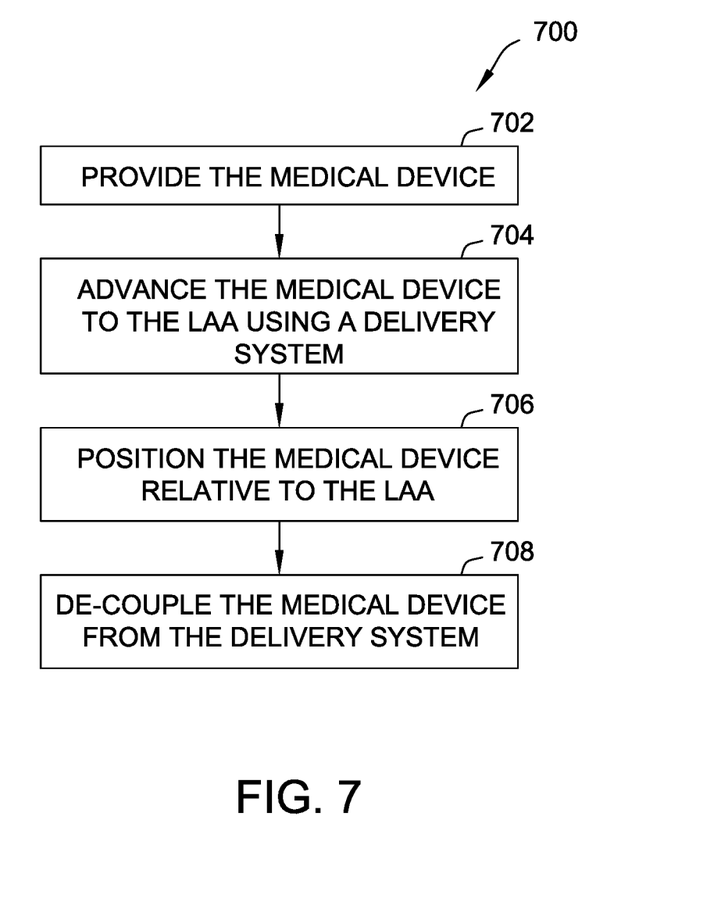
FIG. 7 is a flow diagram of an exemplary method of using a medical device to occlude a target site, in accordance with the present disclosure.

Turning now to FIG. 7, a flow diagram of an exemplary method 700 of using medical device 110 to occlude an LAA in a patient is depicted. In the exemplary embodiment, method 700 includes providing 702 a medical device. As described herein, the medical device includes a proximal and a distal end, wherein the proximal end comprises a disc and the distal end comprises a lobe, wherein the lobe comprises a proximal portion defining a proximal surface of the lobe, a distal portion defining a distal surface of the lobe, and a middle portion connecting and extending between the proximal portion and the distal portion, wherein a first transition between the proximal portion and the middle portion is curved and a second transition between the middle portion and the distal portion is curved, wherein the lobe has an expanded configuration when deployed at the target site and a reduced configuration for delivery to the target site, wherein the disc and lobe are connected by a connecting member, and a plurality of stabilizing wires coupled to the lobe at a radially outer surface of the middle portion, each stabilizing wire comprising a hook portion extending radially outward from the at least one lobe.

Method 700 also includes advancing 704 the medical device to the LAA using a delivery system including a catheter and a delivery cable, positioning 706 the medical device relative to the LAA to occlude blood flow to and from the LAA, and de-coupling 708 the medical device from the delivery cable to deploy the medical device.

Method 700 may include additional, alternative, and/or fewer steps, including those described herein. For example, in some embodiments, positioning 706 the medical device relative to the LAA includes placing the lobe of the medical device within the body of the LAA and the disc outside of the LAA abutted to the adjacent wall surrounding the opening of the LAA to prevent movement of the medical device towards the body of the LAA and to assist in sealing of the abnormality.

Figure 8:
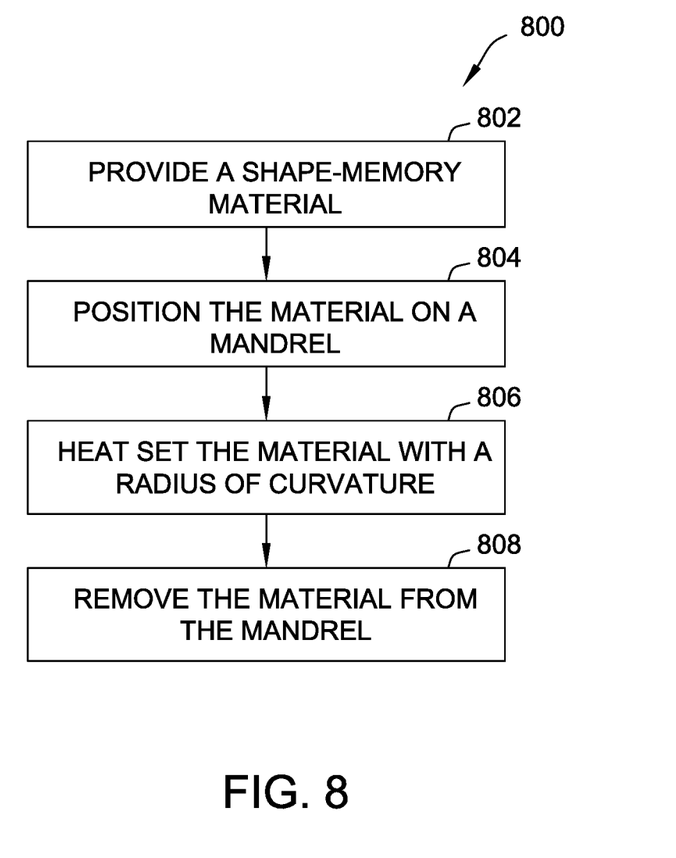
FIG. 8 is a flow diagram of an exemplary method of fabricating a medical device to occlude a target site, in accordance with the present disclosure.

Turning now to FIG. 8, a flow diagram of an exemplary method 800 of fabricating a medical device (e.g., medical device 110) is depicted. As described herein, the medical device includes a proximal and a distal end, wherein the proximal end comprises a disc and the distal end comprises a lobe, wherein the lobe comprises a proximal portion defining a proximal surface of the lobe, a distal portion defining a distal surface of the lobe, and a middle portion connecting and extending between the proximal portion and the distal portion, wherein a first transition between the proximal portion and the middle portion is curved and a second transition between the middle portion and the distal portion is curved, wherein the lobe has an expanded configuration when deployed at the target site and a reduced configuration for delivery to the target site, wherein the disc and lobe are connected by a connecting member, and a plurality of stabilizing wires coupled to the lobe at a radially outer surface of the middle portion, each stabilizing wire comprising a hook portion extending radially outward from the at least one lobe. In the exemplary embodiment, method 800 includes providing 802 a shape-memory material.

Method 800 also includes positioning 804 the shape memory material on a mandrel having a desired shape, size, and radius of curvature for the first transition and a radius of curvature for the second transition, heat setting 806 the shape-memory material to define the expanded preset configuration having the radius of curvature for the first transition and the radius of curvature for the second transition, removing 808 the shape-memory material from the mandrel to obtain the medical device in the expanded preset configuration.

Method 800 may include additional, alternative, and/or fewer steps, including those described herein. For example, in some embodiments, removing 808 the shape-memory material from the mandrel includes cooling the shape-memory material to room temperature.

While embodiments of the present disclosure have been described, it should be understood that various changes, adaptations and modifications may be made therein without departing from the spirit of the disclosure and the scope of the appended claims. Further, all directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. It is intended that all matter contained in the above description or shown in the accompanying drawings shall be interpreted as illustrative only and not limiting. Changes in detail or structure may be made without departing from the spirit of the disclosure as defined in the appended claims.

Many modifications and other embodiments of the disclosure set forth herein will come to mind to one skilled in the art to which this disclosure pertains having the benefit of the teachings presented in the foregoing descriptions and the associated drawings. Therefore, it is to be understood that the disclosure is not to be limited to the specific embodiments described and that modifications and other embodiments are intended to be included within the scope of the appended claims. Although specific terms are employed herein, they are used in a generic and descriptive sense only and not for purposes of limitation.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A medical device for treating a target site, the medical device comprising:
    a proximal end comprising a disc;
    a distal end comprising a lobe, wherein the lobe comprises a proximal portion defining a proximal surface of the lobe, a distal portion defining a distal surface of the lobe, and a middle portion connecting and extending between the proximal portion and the distal portion, wherein a first transition between the proximal portion and the middle portion is curved and a second transition between the middle portion and the distal portion is curved, at least one of the first transition and the second transition having a radius of curvature between 0.001 and 0.150 inches, wherein the lobe has an expanded configuration when deployed at the target site and a reduced configuration for delivery to the target site;
    a connecting member extending between and connecting the disc and the lobe, wherein the proximal surface of the lobe is continuous with the connecting member; and
    a plurality of stabilizing wires coupled to the lobe at a radially outer surface of the middle portion, each stabilizing wire comprising a hook portion that extends radially outward from the lobe in the expanded configuration and the reduced configuration,
    wherein, due to the first and second transition being curved, the middle portion of the lobe resists concave flexion when the lobe is radially compressed at a target site and maintains a radial extension angle of the hooks of the plurality of stabilizing wires during the radial compression.

2. The medical device of claim 1, wherein the medical device is formed from a shape-memory material.

3. The medical device of claim 2, wherein the shape-memory material is selected from the group consisting of Nitinol, stainless steel, and MP34N.

4. The medical device of claim 1, wherein the radius of curvature of at least one of the first transition and the second transition is between 0.025 and 0.150 inches.

5. The medical device of claim 4, wherein the radius of curvature of at least one of the first transition and the second transition is between 0.075 and 0.125 inches.

6. The medical device of claim 1, wherein the radius of curvature of the first transition is approximately equal to the radius of curvature of the second transition.

7. The medical device of claim 1, wherein the radius of curvature of the first transition is less than the radius of curvature of the second transition.

8. The medical device of claim 1, wherein radius of curvature of the first transition is greater than the radius of curvature of the second transition.

9. A delivery system for deploying a medical device to a target site, the delivery system comprising:
    a medical device comprising:
        a proximal end comprising a disc;
        a distal end comprising a lobe, wherein the lobe comprises a proximal portion, a distal portion, and a middle portion, wherein the proximal portion transitions into the middle portion in curved transitions and the middle portion transitions into the distal portion in curved transitions, at least one of the curved transitions having a radius of curvature between 0.001 and 0.150 inches, wherein the lobe has an expanded configuration when deployed at the target site and a reduced configuration for delivery to the target site,
        a connecting member extending between and connecting the disc and the lobe, wherein a proximal surface defined by the distal portion of the lobe is continuous with the connecting member; and
        a plurality of stabilizing wires coupled to the lobe at the middle portion, each stabilizing wire comprising a hook portion that extends radially outward from the lobe in the expanded configuration and the reduced configuration,
        wherein, due to the first and second transition being curved, the middle portion of the lobe resists concave flexion when the lobe is radially compressed at a target site and maintains a radial extension angle of the hooks of the plurality of stabilizing wires during the radial compression; and
    a delivery device comprising:
        a delivery catheter;
        a delivery cable within the delivery catheter and translatable with respect to the delivery catheter; and
        a coupling member configured to couple the proximal end of the medical device to the delivery cable for facilitating at least one deployment of the medical device at the target site.

10. The delivery system of claim 9, wherein the target site is a left atrial appendage (LAA), and wherein, when deployed, the medical device is configured to occlude the LAA.

11. The delivery system of claim 9, wherein the medical device is configured to deploy the lobe in the LAA and the disc outside of the LAA.

12. A method for occluding a Left Atrial Appendage (LAA), the method comprising:

providing a medical device including (i) a proximal end including a disc, (ii) a distal end including a lobe, wherein the lobe includes a proximal portion, a distal portion, and a middle portion, wherein the proximal portion transitions into the middle portion in curved transitions and the middle portion transitions into the distal portion in curved transitions, at least one of the curved transitions having a radius of curvature between 0.001 and 0.150 inches, wherein the lobe has an expanded configuration when deployed at the LAA and a reduced configuration for delivery to the LAA, (iii) a connecting member extending between and connecting the disc and the lobe, wherein a proximal surface defined by the proximal portion of the lobe is continuous with the connecting member, and (iv) a plurality of stabilizing wires coupled to the lobe at the middle portion, each stabilizing wire including a hook portion that extends radially outward from the lobe in the expanded configuration and the reduced configuration, wherein the middle portion of the lobe resists concave flexion when the lobe is radially compressed at a target site and maintains a radial extension angle of the hooks of the plurality of stabilizing wires during the radial compression;

advancing the medical device to the LAA using a delivery system including a catheter and a delivery cable;

positioning the medical device relative to the LAA to occlude blood flow; and de-coupling the proximal end of the medical device from the delivery cable to deploy the medical device.

13. The method of claim 12, wherein positioning comprises placing the lobe within the LAA.

14. The method of claim 12, wherein positioning comprises placing the disc outside of the LAA.

15. The method of claim 14, wherein positioning comprises the disc contacting tissue surrounding the LAA.

16. The method of claim 12, wherein de-coupling comprises deploying the medical device from the delivery system from a constricted configuration to an expanded configuration within the LAA.

* * * * *